(12) United States Patent
Mukai et al.

(10) Patent No.: US 9,561,138 B2
(45) Date of Patent: Feb. 7, 2017

(54) ABSORBENT ARTICLE

(75) Inventors: Hirotomo Mukai, Kagawa (JP);
Yoshihisa Watabe, Kagawa (JP)

(73) Assignee: UNICHARM CORPORATION,
Ehime (JP)

( * ) Notice: Subject to any disclaimer, the term of this patent is extended or adjusted under 35 U.S.C. 154(b) by 407 days.

(21) Appl. No.: 13/641,912

(22) PCT Filed: Apr. 19, 2011

(86) PCT No.: PCT/JP2011/059664
§ 371 (c)(1),
(2), (4) Date: Dec. 20, 2012

(87) PCT Pub. No.: WO2011/132687
PCT Pub. Date: Oct. 27, 2011

(65) Prior Publication Data
US 2013/0102987 A1 Apr. 25, 2013

(30) Foreign Application Priority Data
Apr. 19, 2010 (JP) .................................. 2010-096531

(51) Int. Cl.
*A61F 13/496* (2006.01)
*A61F 13/49* (2006.01)
*A61F 13/539* (2006.01)

(52) U.S. Cl.
CPC ...... *A61F 13/49011* (2013.01); *A61F 13/4902* (2013.01); *A61F 13/496* (2013.01); *A61F 13/49019* (2013.01); *A61F 13/539* (2013.01)

(58) Field of Classification Search
CPC .......................... A61F 13/539; A61F 13/49011
(Continued)

(56) References Cited

U.S. PATENT DOCUMENTS 5,749,865 A * 5/1998 Yamamoto ............ A61F 13/496
604/385.29
6,364,863 B1 4/2002 Yamamoto et al.
(Continued)

FOREIGN PATENT DOCUMENTS

AU 2008294255 A1 3/2009
CA 2707003 A1 6/2009
(Continued)

OTHER PUBLICATIONS

Extended European Search Report issued Jan. 22, 2014, corresponds to European patent application No. 11772020.1.
International Search Report and Written Opinion corresponding to PCT/JP2011/059664, dated Jul. 19, 2011.
Office Action issued Feb. 27, 2014, corresponds to Chinese patent application No. 201180019790.2.
(Continued)

*Primary Examiner* — Paula L Craig
(74) *Attorney, Agent, or Firm* — Hauptman Ham, LLP

(57) ABSTRACT

In the disclosed absorbent article, in a first region, a first elastic member extends linearly in the widthwise direction, in a second region, a second elastic member extends linearly in the widthwise direction, the elongational stress of the first elastic member is greater than the elongational stress of the second elastic member, and the length in the widthwise direction of the joining region that is of both the main body of an absorbent body and a chassis in the first region is configured in a manner so as to be shorter than the length in the widthwise direction of the joining region that is of both the main body of the absorbent body and the chassis in the second region.

11 Claims, 9 Drawing Sheets

(58) Field of Classification Search
USPC .................. 604/85.3, 396, 385.24, 385.29
See application file for complete search history.

(56) References Cited

U.S. PATENT DOCUMENTS

| | | | |
|---|---|---|---|
| 2002/0045872 A1* | 4/2002 | Shimada | A61F 13/49011 |
| | | | 604/385.3 |
| 2002/0152540 A1* | 10/2002 | Van Gompel et al. | 2/406 |
| 2005/0004549 A1* | 1/2005 | Maas | A61F 13/49009 |
| | | | 604/385.29 |
| 2005/0085784 A1* | 4/2005 | LeMinh | A61F 13/539 |
| | | | 604/387 |
| 2005/0148965 A1* | 7/2005 | Richlen | A61F 13/15756 |
| | | | 604/367 |
| 2010/0106123 A1* | 4/2010 | Fukae | 604/373 |
| 2010/0252178 A1 | 10/2010 | Takino et al. | |
| 2010/0286646 A1 | 11/2010 | Takino et al. | |
| 2012/0302417 A1* | 11/2012 | Gouda | A61F 13/15593 |
| | | | 493/346 |
| 2012/0302985 A1* | 11/2012 | Mukai | A61F 13/15593 |
| | | | 604/385.24 |

FOREIGN PATENT DOCUMENTS

| | | |
|---|---|---|
| JP | 956747 A | 3/1997 |
| JP | 09056746 A | 3/1997 |
| JP | 09056747 A | 3/1997 |
| JP | 2004298399 A | 10/2004 |
| JP | 2008132023 A | 6/2008 |
| JP | 2008194160 A | 8/2008 |
| JP | 2008194161 A | 8/2008 |
| JP | 2009061046 A | 3/2009 |
| JP | 200969343 A | 4/2009 |
| WO | WO 2008108270 A1 * | 9/2008 |
| WO | 2009031359 A1 | 3/2009 |
| WO | WO 2009031393 A1 * | 3/2009 |

OTHER PUBLICATIONS

Office Action issued Feb. 9, 2015, corresponding to Australian patent application No. 2011243572.
Office Action mailed Jun. 16, 2015, corresponding to Japanese patent application No. 2012-511674.

* cited by examiner

ABSORBENT ARTICLE

RELATED APPLICATIONS

The present application is a National Phase of International Application Number PCT/JP2011/059664, filed Apr. 19, 2011, and claims priority from Japanese Application Number 2010-096531, filed Apr. 19, 2010.

TECHNICAL FIELD

The present invention relates to an absorbent article.

BACKGROUND ART

Conventionally, there are known a chassis having a front waistline portion, a rear waistline portion, and a crotch portion, and an absorbent article having an absorbent body provided from the crotch portion across the front waistline portion and rear waistline portion.

In such an absorbent article, there is known a technique in which by changing a level of extension stress for each of several types of elastic members to be arranged in the waistline portion, pressure on a wearer due to a tightening force is prevented while maintaining a force exerted to keep wearing the absorbent article (for example, see Latent Literature 1).

CITATION LIST

Patent Literature

Patent Literature 1: Japanese Patent Application Publication No. 2004-298399

SUMMARY OF INVENTION

However, the applicants faced the following problem as regard the above absorbent article.

In such an absorbent article, a shape of the absorbent body provided in the rear waistline portion is greatly changed between a state when the wearer is sitting and a state when he or she is standing, thereby leading to a problem that a large gap is generated between the wearer and the absorbent body.

Herein, in order to solve such a problem, in a case of increasing a contact of the absorbent body provided in the rear waistline portion to the wearer by making an extension stress of an elastic member provided in the front waistline portion larger than an extension stress of an elastic member provided in the rear waistline portion, there is a problem that wrinkles are easily caused in the absorbent body provided in the front waistline portion.

Thus, the present invention has been achieved in view of the aforementioned problem, and an object thereof is to provide an absorbent article which is capable of reducing wrinkles caused in the absorbent body arranged in the front waistline portion while increasing a contact of the absorbent body arranged in the rear waistline portion to the wearer.

A first feature of the present invention is summarized as an absorbent article, comprising: a chassis; and an absorbent body, wherein the chassis includes a front waistline portion, a rear waistline portion, and a crotch portion provided between the front waistline portion and the rear waistline portion, respective one of both-side edges of the front waistline portion and respective one of both-side edges of the rear waistline portion are configured to be joined, the absorbent body is provided from the crotch portion across the front waistline portion and the rear waistline portion, a first portion is provided at a leg hole opening side of a portion to which the both-side edges are joined, within the front waistline portion, and which extends from one edge to the other edge in a width direction, a second portion is opposed to the first portion, within the rear waistline portion, at the first portion, a first elastic member extends in a straight line in the width direction, at the second portion, a second elastic member extends in a straight line in the width direction, an extension stress of the first elastic member is larger than an extension stress of the second elastic member, and a length in the width direction of a joining portion between the chassis and the absorbent body at the first portion is shorter than a length in the width direction of the joining portion between the chassis and the absorbent body at the second portion.

DESCRIPTION OF EMBODIMENTS (First Embodiment of the Present Invention)

With reference to FIG. 1 to FIG. 7, an absorbent article 1 according to a first embodiment of the present invention will be described. The absorbent article 1 according to the embodiment is a pant-type diaper, a water-absorbent underwear, etc.

Figure 1:
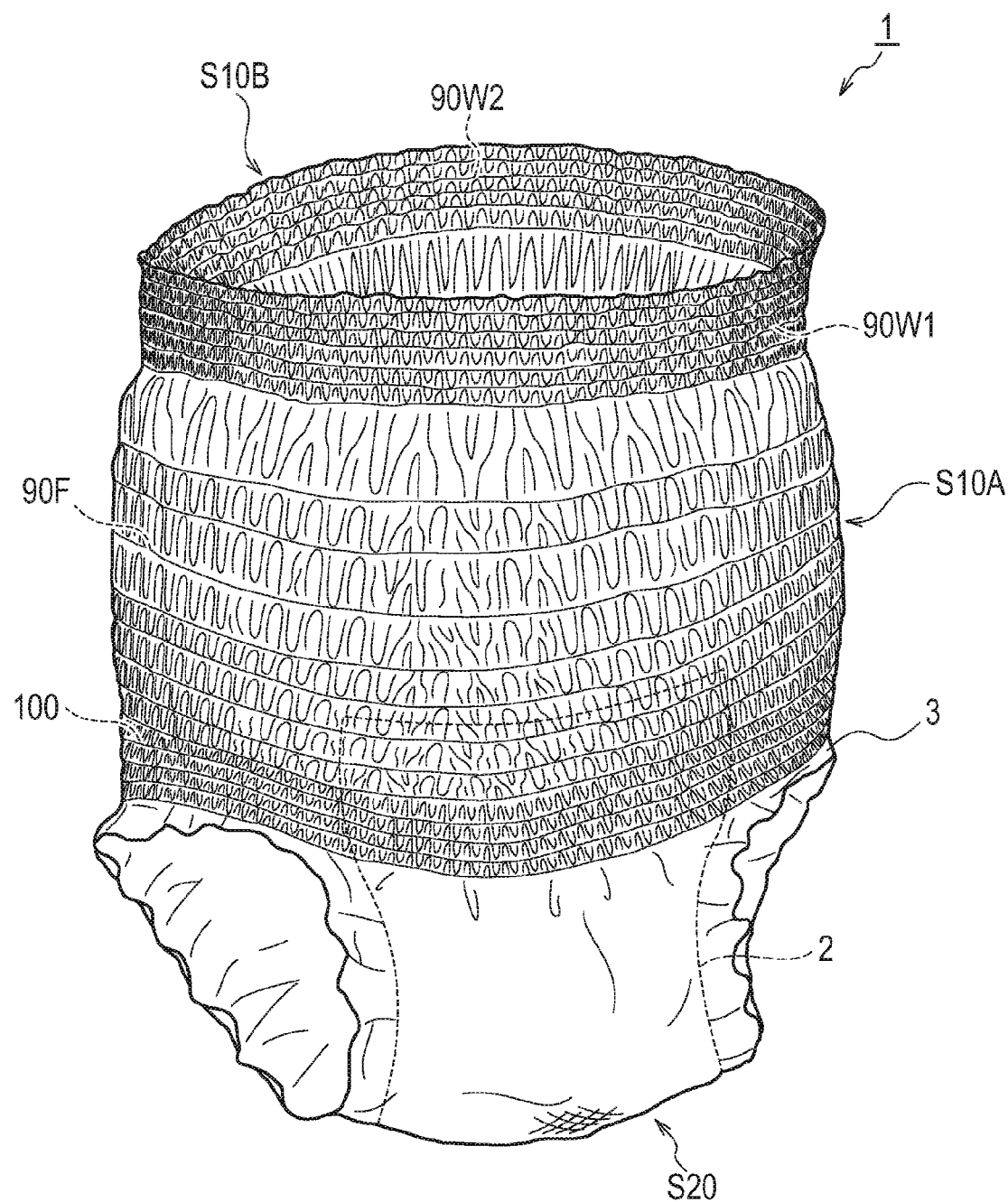
FIG. 1 is an external view of an absorbent article according to a first embodiment of the present invention.

FIG. 1 is an external view of the absorbent article 1 according to the embodiment. As shown in FIG. 1, the absorbent article 1 according to the embodiment has a chassis 3 and an absorbent body 2.

Specifically, as shown in FIG. 2 to FIG. 5, the absorbent body 2 is configured by an absorbent body-side topsheet 10 that is a liquid-permeable sheet in contact with the skin of the wearer; an absorbent core 20; and an absorbent body side-backsheet 30 that is a liquid-impermeable sheet.

A sheet made from a hydrophilic nonwoven cloth made of fibers such as polyolefin and polyethylene terephthalate (PET), which is manufactured by methods such as spun bonding and air-through can be used as the absorbent body-side topsheet 10. A sheet made of a water-resistive film such as polyethylene (PE) can be used as the absorbent body-side backsheet 30.

For example, the absorbent body-side topsheet 10 is 25 g/m² of air-through nonwoven cloth, and the absorbent body-side backsheet 30 is 22 g/m² of moisture-permeable polyethylene film.

Figure 4:
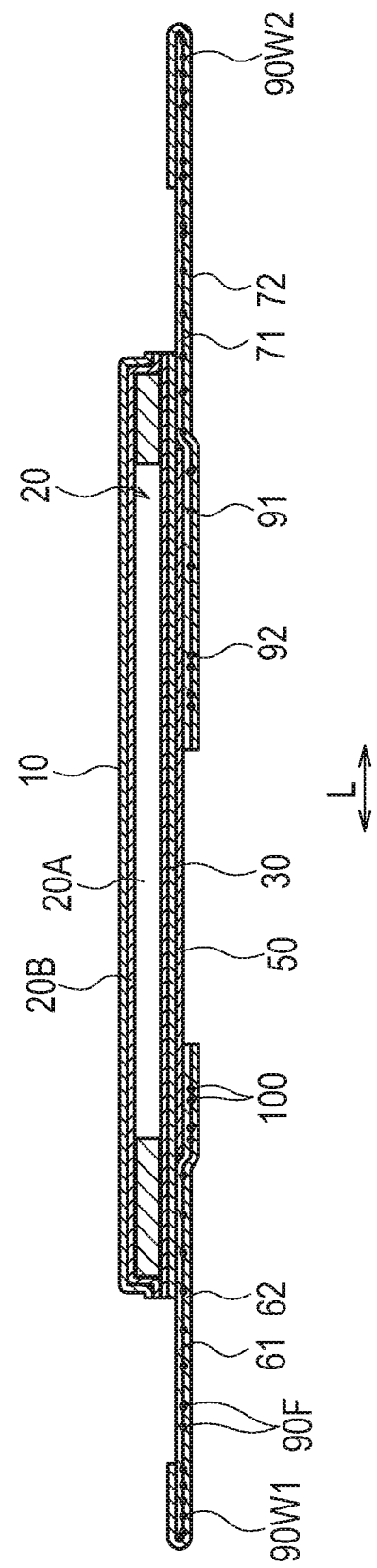
FIG. 4 is a cross-sectional view along a line A-A in the plan view of the absorbent article according to the first embodiment of the present invention.
Figure 5:
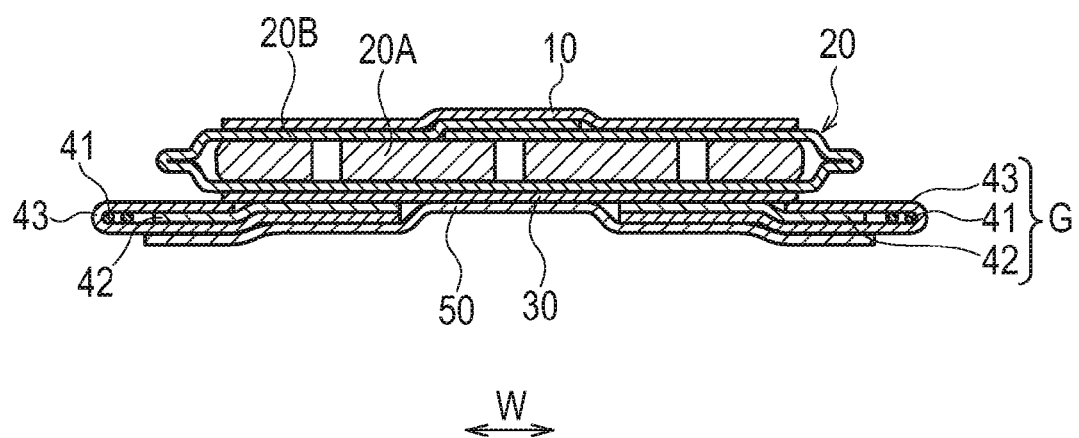
FIG. 5 is a cross-sectional view along a line B-B in the plan view of the absorbent article according to the first embodiment of the present invention.

The absorbent core 20 is generated, for example, by wrapping a mixture 20A of ground pulp (for example, 200 g/m²) and a high absorbent polymer (for example, 200 g/m²) with a wrapping sheet 20B, as shown in FIG. 4 and FIG. 5.

A sheet made from a hydrophilic nonwoven cloth made of fibers such as polyolefin and polyethylene terephthalate, which is manufactured by methods such as spun bonding and air-through can be used as the wrapping sheet 20B. For example, the wrapping sheet 20B is 13 g/m² of SMS nonwoven cloth.

The absorbent body-side topsheet 10, the absorbent body-side backsheet 30, and the wrapping sheet 20B are mutually joined by a hot-melt adhesive (for example, spiral HMA).

For example, the basis weight of the hot-melt adhesive is 1.5 to 10 g/m². Furthermore, besides spiral coating, methods such as slot coating, control seam, beading, and curtain coater may be used for joining by the hot-melt adhesive.

Note that the absorbent core 20 is a thin absorber with a thickness of approximately 2.0 mm, and with less ruggedness on the surface thereof.

As shown in FIG. 2 to FIG. 5, a barrier cuffs G is provided at both sides in the longitudinal direction L of the absorbent body 2. In other words, the barrier cuffs G is joined with both sides in the width direction W of the absorbent body-side backsheet 30.

The barrier cuffs G is configured by thread-shaped elastic members 41 for the barrier cuffs, a water-resistant film 42, and a hydrophobic nonwoven cloth 43.

As shown in FIG. 5, at the upright supporting point side (that is, the inner side in the width direction W) of the barrier cuffs 30, the position of the end of the water-resistant film 42 and the position of the end of the hydrophobic nonwoven cloth 43 almost match, and at the free end of the barrier cuffs G (that is, the end of the outer side in the width direction W), the hydrophobic nonwoven cloth 43 is folded back such that it sandwiches the elastic members 41 for the barrier cuffs. Furthermore, the water-resistant film 42 does not reach up to the free end of the barrier cuffs G.

A fabric made from a hydrophobic nonwoven cloth made of fibers such as polyolefin and polyethylene terephthalate, which is manufactured by methods such as spun bonding can be used as the hydrophobic nonwoven cloth 43. For example, the hydrophobic nonwoven cloth 43 is 15 g/m² of hydrophobic SMS nonwoven cloth.

Furthermore, a film made from polyethylene, polyethylene terephthalate, and the like can be used as the water-resistant film 42. For example, 18 g/m² of moisture-permeable polyethylene film can be used.

The elastic members 41 for the barrier cuffs may be configured by natural rubber, synthetic rubber, and spandex, etc. For example, the elastic members 41 for the barrier cuffs comprise two 620-tex spandex threads each at the left and right sides, which are fixed by a hot-melt adhesive coated on the hydrophobic nonwoven cloth 43 with the slit nozzle method when extended with an extension rate of 2.2 times.

Furthermore, as shown in FIG. 2 to FIG. 5, the chassis 3 is configured by a center sheet 50, a front waistline sheet 60, and a rear waistline sheet 70.

Figure 3:
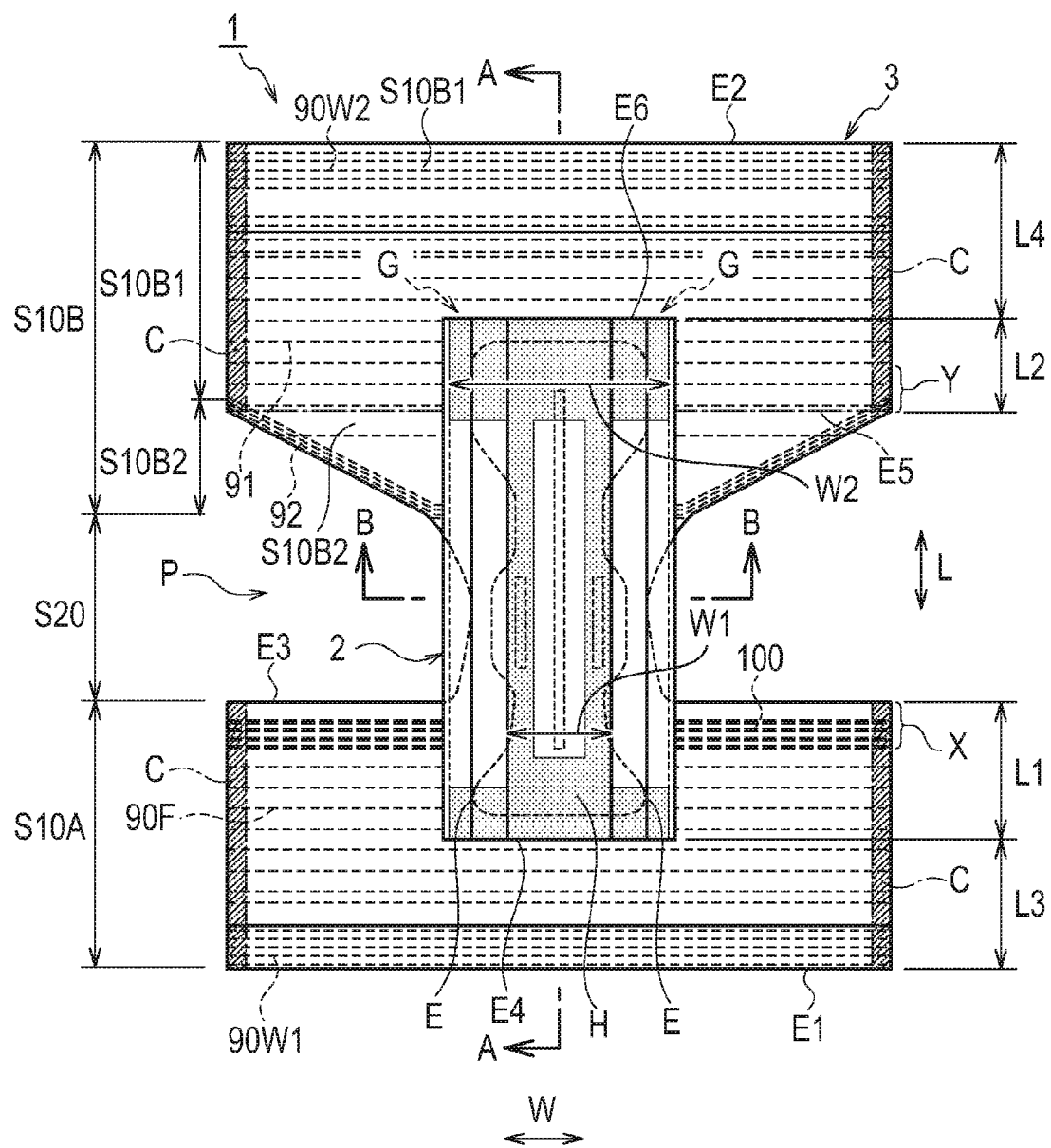
FIG. 3 is a plan view of the absorbent article according to the first embodiment of the present invention.

Therefore, as shown in FIG. 3, the chassis 3 comprises a front waistline portion S10A corresponding to the front waistline sheet 60, a rear waistline portion S10B corresponding to the rear waistline sheet 70, and a crotch portion S20 provided between the front waistline portion S10A and rear waistline portion S10B.

Thus, as shown in FIG. 2 to FIG. 5, the absorbent body 2 is provided at the skin contact surface side of the absorbent article 1 of the chassis 3 from the crotch portion S20 across the front waistline portion S10A and rear waistline portion S10B.

Note that as shown in FIG. 3, in the front waistline portion S10A and rear waistline portion S10B, the absorbent body 2 is provided in the central portion in the width direction W.

Furthermore, in the absorbent article 1 according to the embodiment, the configuration is such that both-side edges C of the front waistline portion S10A and both-side edges C of the rear waistline portion S10B are joined.

The center sheet 50 is arranged at the skin contact surface side of the front waistline sheet 60 and the rear waistline sheet 70, and is, for example, configured by 15 g/m² of SMS nonwoven cloth made from polypropylene (PP).

Further, the front waistline sheet 60 is configured by a front waistline topsheet 61 and a front waistline backsheet 62.

Here, between the front waistline topsheet 61 and the front waistline backsheet 62, elastic members 90W1 for hip gathers, elastic members 90F for front waistline gathers, and elastic members 100 for leg hole gathers are retained in the extended condition.

Further, as shown in FIG. 4, the front waistline backsheet 62 is folded back towards the inner side in the longitudinal direction L at the end in the longitudinal direction L, and the elastic members 90W1 for the hip gathers are retained in the extended condition in the front waistline backsheet 62 in the folded-back portion.

Similarly, the rear waistline sheet 70 is configured by a rear waistline topsheet 71 and a rear waistline backsheet 72.

Here, between the rear waistline topsheet 71 and the rear waistline backsheet 72, elastic members 90W2 for the hip gathers, elastic members 91 for the rear waistline gathers, and elastic members 92 for the leg hole gathers are retained in the extended condition.

Further, as shown in FIG. 4, the rear waistline backsheet 72 is folded back towards the inner side in the longitudinal direction L at the end in the longitudinal direction L, and the elastic members 90W2 for the hip gathers are retained in the extended condition in the rear waistline backsheet 72 in the folded-back portion.

A sheet made from a hydrophobic nonwoven cloth such as polyolefin and polyethylene terephthalate, which is manufactured by methods such as spun bonding and air-through can be used as the front waistline sheet 60 and the rear waistline sheet 70.

Further, the basis weight of the front waistline topsheet 61, the basis weight of the front waistline backsheet 62, the basis weight of the rear waistline topsheet 71, and the basis weight of the rear waistline backsheet 72 are each desired to be 13 to 30 g/m².

For example, the front waistline topsheet 61 and the rear waistline topsheet 71 are 15 g/m² of SMS nonwoven cloths made from polypropylene, and the front waistline backsheet 62 and the rear waistline backsheet 72 are 17 g/m² of spun bond nonwoven cloths made from polypropylene.

For example, the extension rate of each of the elastic members 90W1, 90W2 for the hip gathers is 2.7 times, and the number of each of the elastic members 90W1, 90W2 for the hip gathers is five.

For example, each of the elastic members 90W1, 90W2 for the hip gathers is configured by spandex, and has a thickness of 940 dtex.

Figure 2:
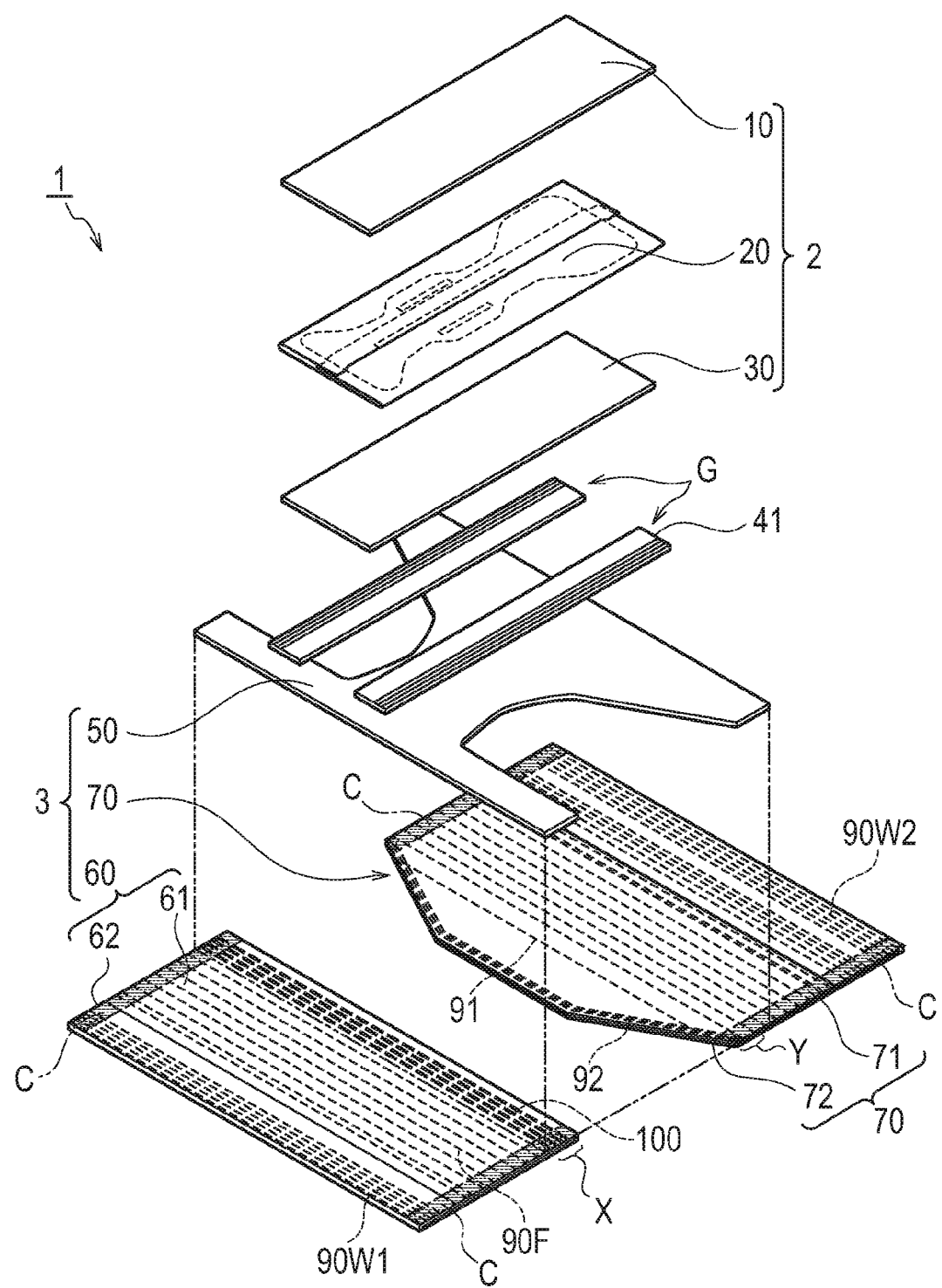
FIG. 2 is an exploded view of the absorbent article according to the first embodiment of the present invention.

As shown in FIG. 2, the elastic members 100 for the leg hole gathers (that is, first elastic members) are arranged in a straight line between one end and the other end in the width direction W at the front waistline topsheet 61 and the front waistline backsheet 62.

That is, as shown in FIG. 3, the elastic members 100 for the leg hole gathers (that is, the first elastic members) extend in a straight line in the width direction W at a first portion X within the front waistline portion S10A.

Further, as shown in FIG. 2, at the rear waistline portion S10B, the elastic members 91 for the rear waistline gathers (that is, second elastic members) are arranged in a straight line between one end and the other end in the width direction W at the rear waistline topsheet 71 and the rear waistline backsheet 72.

That is, as shown in FIG. 3, the elastic members 91 for the rear waistline gathers (that is, the second elastic members) extend in a straight line in the width direction at a second portion Y within the rear waistline portion S10B.

Herein, the first portion X is a portion which is provided at a leg hole opening P side of a portion to which the both-side edges C are joined, within the front waistline portion S10A, and which extends from one edge C at one side to the edge C at the other side in the width direction W. Further, the second portion Y is a portion which is opposed to the first portion X, within the rear waistline portion S10B.

As shown in FIG. 3, the rear waistline portion S10B has a hip portion S10B1 and a leg hole portion S10B2.

The hip portion S10B1 is a portion in which the both-side edges C are joined with the both-side edges C of the front waistline portion S10A and which extends from the edge C at one side to the edge C at the other side in the width direction W. The leg hole portion S10B2 is the portion closer to the crotch portion S20 than the hip portion S10B1.

Therefore, the elastic members 91 for the rear waistline gathers extend in a straight line in the width direction W at both of the hip portion S10B1 and the leg hole portion S10B2 within the rear waistline portion S10B.

Within the front waistline portion S10A, the elastic members 90F for the front waistline gathers extend in a straight line in the width direction W at the outside in the longitudinal direction L of the elastic members 100 for the leg hole gathers. Herein, part of the elastic members 90F for the front waistline gathers extends in the width direction W so as to cross the absorbent body 2.

Within the front waistline portion S10A, further, the elastic members 90W1 for the hip gathers extend in a straight line in the width direction W at the outside in the longitudinal direction L of the elastic members 90F for the front waistline gathers.

Within the rear waistline portion S10B, the elastic members 92 for the leg hole gathers extend along the edge at the leg hole opening P side at the leg hole portion S10B2.

At the hip portion S10B1 within the rear waistline portion S10B, the elastic members 90W2 for the hip gathers extend in a straight line in the width direction W at the outside in the longitudinal direction L of the elastic members 91 for the rear waistline gathers.

Herein, the extension stress of the elastic members 100 for the leg hole gathers is larger than the extension force of the elastic members 91 for the rear waistline gathers which extend in the width direction W so as to cross the absorbent body.

For example, the extension rate of the elastic members 100 for the leg hole gathers is 1.3 times larger at the inward in the width direction W than the extension rate of an edge E of the absorbent body 2, and is 2.5 times larger at the outward in the width direction W than the extension rate of the edge E of the absorbent body 2. Further, the number of elastic members 100 for the leg hole gathers is four.

The extension rate of the elastic members 100 for the leg hole gathers may be the same all over in the width direction W, for example, 2.0 times.

Further, the elastic members 100 for the leg hole gathers are configured by spandex, and have a thickness of 620 dex.

On the other hand, the extension rate of the elastic members 91 for the rear waistline gathers which extend in the width direction W so as to cross the absorbent body 2 is 1.5 times and the number of these elastic members 91 for the rear waistline gathers is six.

The elastic members 91 for the rear waistline gathers which extend in the width direction W so as not to cross the absorbent body 2 is 2.2 times and the number of these elastic members 91 for the rear waistline gathers is seven.

Further, the elastic members 91 for the rear waistline gathers are configured by spandex, and each of the elastic members 91 for the rear waistline gathers has a thickness of 620 dex.

Therefore, the extension stress of the elastic members 100 for the leg hole gathers at the inside in the width direction W of the edge E in the width direction of the absorbent body 2 is smaller than the extension stress of the elastic members 100 for the leg hole gathers at the outside in the width direction W of the edge E in the width direction of the absorbent body 2.

Further, the extension stress of the elastic members 100 for the leg hole gathers at the outside in the width direction W of the edge E in the width direction of the absorbent body 2 is larger than the extension stress of the elastic members 91 for the rear waistline gathers at the outside in the width direction W of the edge E in the width direction of the absorbent body 2. The elastic members 100 for the leg hole gathers and the elastic members 91 for the rear waistline gathers have preferably a stress difference of 20% or more, more preferably, a stress difference of 1.2 times to 10.0 times.

The extension stress of the elastic members 90F for the front waistline gathers which extend in the width direction W so as to cross the absorbent body 2 at an outside in the longitudinal direction L of the first portion X is smaller than the extension stress of the elastic members 100 for the leg hole gathers. The elastic members 90F for the front waistline gathers and the elastic members 100 for the leg hole gathers have preferably a stress difference of 10% or more, more preferably a stress difference of 1.1 times to 7.0 times.

Herein, the extension rate of the elastic members 90F for the front waistline gathers which extend in the width direction W so as to cross the absorbent body 2 is 1.5 times, and the number of these elastic members 91 for the front waistline gathers is four.

Further, the extension rate of the elastic members 90F for the front waistline gathers which extend in the width direction W so as not to cross the absorbent body 2 is 2.2 times, and the number of these elastic members 91 for the front waist line is four.

For example, the elastic members 90F for the front waistline gathers are configured by spandex, and have a thickness of 620 dex.

The extension stress of the elastic members 100 for the leg hole gathers is larger than the extension stress of the elastic members 92 for the leg hole gathers. For example, the extension stress of the elastic members 92 for the leg hole gathers is 1.8 times. The elastic member 100 for the leg hole gathers and the elastic members 92 for the leg hole gathers have preferably a stress difference of 10% or more, more preferably a stress difference of 1.1 times to 7.0 times.

Figure 6:
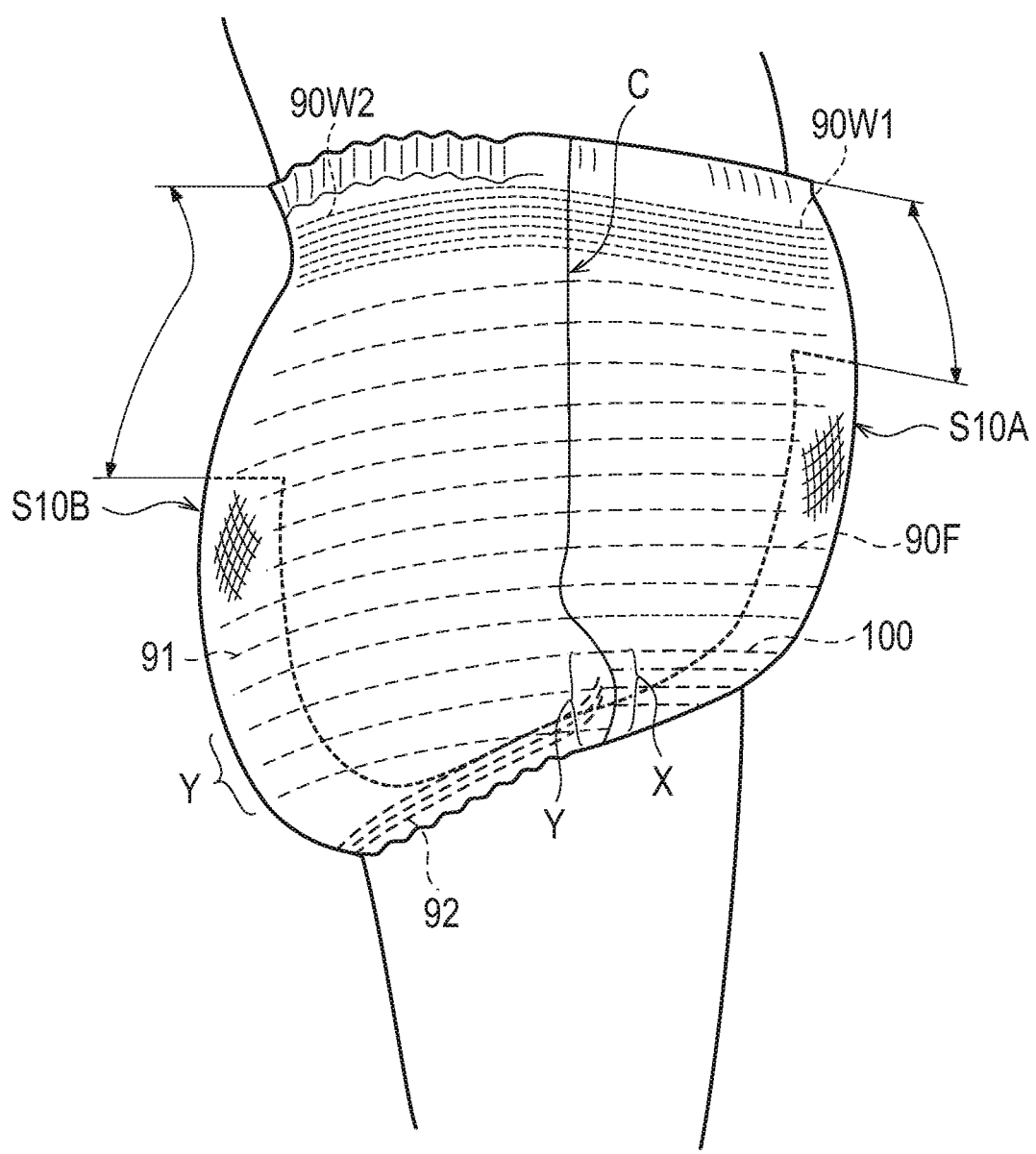
FIG. 6 is an external view as seen from a lateral side, for showing a state in which the absorbent article according to the first embodiment of the present invention is worn.

FIG. 6 is an external view as seen from a lateral side, for showing a state in which the absorbent article 1 according to the present embodiment is worn.

As shown in FIG. 6, in the absorbent article 1 according to the present embodiment, the extension stress of the elastic members 100 for the leg hole gathers is larger than the extension stress of the elastic members 91 of the rear waistline gathers, so that at the time of wearing the absorbent article 1, the both-side edges C of the front waistline portion S10A and the both-side edges C of the rear waistline portion S10B, which are joined together, are pulled up toward the front waistline portion S10A side.

As a result, the absorbent body 2 arranged within the rear waistline portion S10B can be adhered more closely to the wearer.

Further, the extension stress at the portion in which the thread-shaped elastic members are arranged can be measured by the following procedure. Note that at the portion in which the thread-shaped elastic members are arranged, the thread-shaped elastic members are sandwiched between, for example, a pair of clothing fabrics such as nonwoven cloth.

(1) In a loose state (a non-extension state), the part (measurement object part) in which the thread-shaped elastic members are arranged is cut out. For example, the measurement object part has a length of 150 mm in a direction (hereinafter, referred to as an extension direction) in which the thread-shaped elastic members extend, and has a width of 25 mm in a direction orthogonal to the extension direction.

(2) The measurement object part is extended in the extension direction until when it achieves a natural length. Subsequently, a pair of markers is assigned to the measurement object part, at a predetermined marking interval (natural length) in the extension direction. For example, the predetermined marking interval (natural length) of the pair of markers is 100 mm.

(3) The measurement object part is left in the loose state. For example, under the environment at a constant temperature (20 to 23 degrees Celsius) and a constant humidity (60 to 65% RH), the measurement object part is left for 24 hours. The reason why the measurement object part is left for 24 hours under the environment at constant temperature and humidity is because it is necessary to leave the part under certain conditions until when stress recovery becomes stable. Further, the tensile test described below is also performed under the same environment at a constant temperature and humidity so as to avoid the influence on elasticity.

(4) In the loose state, a tensile tester zips up the both sides of the measurement object part in accordance with the pair of markers in the extension direction. Subsequently, the tensile tester extends the measurement object part until when an interval between the markers achieves a predetermined marking interval (measurement). The predetermined marking interval (measurement) is narrower than the predetermined marking interval (natural length). For example, the predetermined marking interval (measurement) is 90% of the predetermined marking interval (natural length). Further, the extension velocity of the measurement object part is 100 mm/min. Note that the reason why the predetermined marking interval (measurement) is narrower than the predetermined marking interval (natural length) is to prevent damage on clothing fabric for sandwiching the thread-shaped elastic members. Further, as a tensile tester, for example, an autograph type tensile tester made by Shimadzu Corporation (Model: AG-I) can be used.

(5) In a state where the measurement object part is extended until when an interval between the markers achieves the predetermined interval (measurement), a stress (extension stress) exerted on the measurement object part is measured. Note that a unit of extension stress is N, for example.

However, in a case of making a comparison in the extension stress, it is to be noted that there is a case where the number of thread-shaped elastic members contained in the measurement object part is different. Specifically, gathers a stress of which is desired to be measured are cut out by a gather width (for example, gathers configured by four elastic members), and the whole stress of the cut-out gathers is measured. The measured whole stress is converted into a stress per 10 mm (1 cm) in accordance with the cut-out gather width, and the converted value is set to a stress of gathers. A comparison is made to the extension rates converted as described above.

For example, in a case where the gathers taken out by a width of 25 mm contain four elastic members, a distance between the outermost sides of these four elastic members (between the outward end in the width direction of the first elastic member and the outward end in the width direction of the fourth elastic member out of these four elastic members) is 15 mm, and a measured value is A, a stress value $X1$ per unit width is determined by $X1 = A \times 10/15$ (N/cm). In a case where an interval between the elastic members (between the outermost sides) is partially different in the measurement object part, an approximate average value of intervals in the measurement object part is determined and used for calculation.

Further, in a case where the elastic members are not in a thread shape but in a sheet shape, a width of the elastic members contained in an extraction width is determined (C mm), and a stress per unit width can be determined by dividing a measured value by the determined width. Herein, in a case where the measured value is A', a stress value $X2$ per unit width is determined by $X2 = A' \div C \times 10$ (N/cm).

Note that in a case of extracting measurement samples, it is required to be careful not to include elastic members other than the elastic members to be measured.

Further, the absorbent article 1 according to the present embodiment is configured so that a length in the width direction W of a joining portion H between the chassis 3 and the absorbent body 2 at a first portion X is shorter than a length in the width direction W of the joining portion H between the chassis 3 and the absorbent body 2 at a second portion Y.

In the example shown in FIG. 3, a length in the width direction W of the joining portion H between the chassis 3 and the absorbent body 2 at the first portion X is "W1" while a length in the width direction W of the joining portion H between the chassis 3 and the absorbent body 2 at the second portion Y is "W2". The length W1 (ventral side) is 0 to 200 mm, preferably 30 to 150 mm. The length W2 (buttock side) is 100 to 300 mm, preferably 120 to 220 mm. Note that a width of the absorbent body 2 is 120 to 300 mm and particularly, a size of 150 to 250 mm is preferably adopted. In addition, in the present embodiment, the length W1 is 90 mm and the length W2 is 170 mm (in a case of the absorbent body 2 having a width of 180 mm).

According to the above configuration, at the front waistline portion S10A, a length in the width direction W of the joining portion between the elastic members 100 for the leg hole gathers within the chassis 3 and the absorbent body is made narrow, thereby achieving reduction in wrinkles caused in the absorbent body 2 arranged in the front waistline portion S10A.

According to the above configuration, the extension stress is made large in the front waistline portion S10A and small in the front rear waistline portion S10B, so that the rear waistline portion S10B is more easily stretched as compared with the front waistline portion S10A, and a width of the absorbent body 2 at the rear waistline portion S10B can be made larger by extending the length in the width direction of the joining portion between the absorbent body 2 and the elastic members 91 for the rear waistline gathers within the chassis 3. As a result, an absorption area can be increased to improve absorption performance without the liquid flowing out from grooves of wrinkles caused in the absorbent article 2 and also, the feeling of wearing the absorbent article 2 can be improved.

According to the above configuration, in the joining portion H at the front waistline portion S10A, a range of wrinkles formed in the absorbent article 2 can be decreased.

According to the above configuration, in spite of a large extension rate of the elastic members 100 for the leg hole gathers, shrinkage in the width direction of the absorbent body 2 can be decreased, thereby not damaging the absorbent performance.

Further, the absorbent article 1 according to the present embodiment is configured so that a distance L1 between an edge E3 at the leg hole opening P side at the first portion X and an edge E4 in the longitudinal direction L of the absorbent body 2 (or the absorbent core 20) within the front waistline portion S10A is longer than a distance L2 between an edge E5 at the leg hole opening P side of the second portion Y and an edge E6 in the longitudinal direction L of the absorbent body 2 (or the absorbent core 20) within the rear waistline portion S10B.

In other word, the absorbent article 1 according to the present embodiment is configured so that a distance L3 between an edge E1 at the outside in the longitudinal direction L of the front waistline portion S10A and the edge E4 in the longitudinal direction L of the absorbent body 2 (or the absorbent core 20) within the front waistline portion S10A is shorter than a distance L4 between an edge E2 at the outside in the longitudinal direction L of the rear waistline portion S10B and an edge E6 in the longitudinal direction L of the absorbent body 2 (or the absorbent core 20) within the rear waistline portion S10B.

Note that as shown in FIG. 2 to FIG. 5, each of the members configuring the above-mentioned center sheet 50, the front waistline sheet 60, and the rear waistline sheet 70 is configured to be joined by a heat seal, a sonic seal, a hot-melt adhesive, and the like.

Furthermore, the front waistline topsheet 61 and the front waistline backsheet 62 are joined by a hot-melt adhesive that is coated directly onto the elastic members 90F for the front waistline gathers and the elastic members 100 for the leg hole gathers, and the rear waistline topsheet 71 and the rear waistline backsheet 72 are joined by a hot-melt adhesive that is coated directly onto the elastic members 91 for the rear waistline gathers.

That is, in the absorbent article 1 according to the embodiment, the hot-melt adhesive is not coated onto the front waistline topsheet 61 and the front waistline backsheet 62.

According to the configuration, the softness of the front waistline topsheet 61 and the front waistline backsheet 62 can be improved.

Also, the hot-melt adhesive is not coated onto the rear waistline topsheet 71 and the rear waistline backsheet 72 in the portion where the elastic members 91 for the rear waistline gathers are joined. According to the configuration, the softness of the rear waistline topsheet 71 and the rear waistline backsheet 72 in the portion can be improved.

On the other hand, the hot-melt adhesive may be coated through spiral coating along the pattern of the elastic members 92 for the leg hole gathers onto the rear waistline backsheet 72 in the portion where the elastic members 92 for the leg hole gathers are joined.

Note that at locations where the above-mentioned interval of the elastic members is, for example, more than 10 mm, the hot-melt adhesive may be coated partially with coating methods such as spiral coating and control seam.

Rubber adhesives made from styrene-isoprene-styrene (SIS), styrene-butadiene-styrene (SBS), and styrene-ethylene/butylene-styrene (SEBS), as well as olefin adhesives are used as the hot-melt adhesive.

Next, some of the methods of manufacturing the absorbent article 1 according to the embodiment are described with reference to FIG. 7. Note that as far as the methods that are not described in FIG. 7 are concerned, the existing methods can be used.

Figure 7:
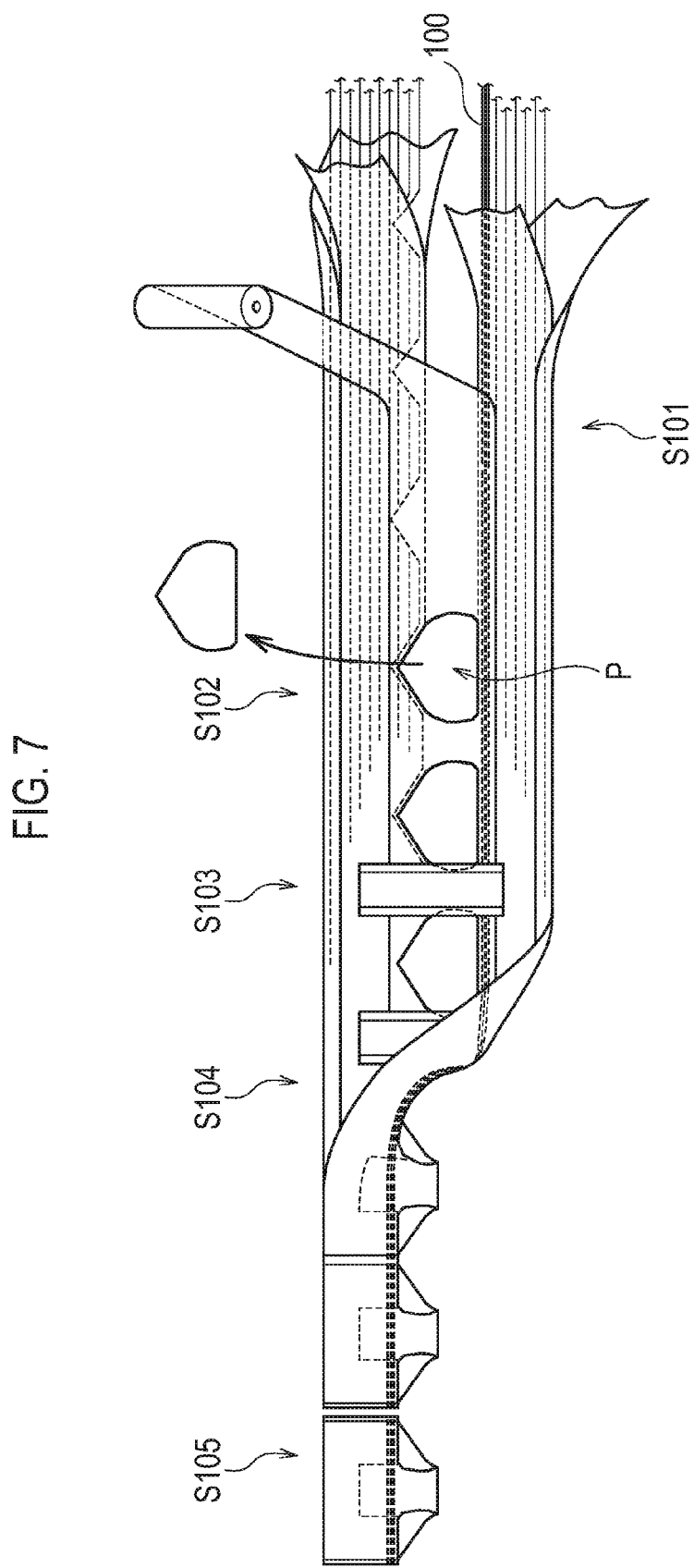
FIG. 7 is a view for explaining a method of manufacturing the absorbent article according to the first embodiment of the present invention.

As shown in FIG. 7, in step S101, the chassis 3 is generated.

Herein, in step S101, in order to establish the above relationship, the extension rate is adjusted for the elastic members 90W1 for the hip gathers, the elastic members 90F for the front waistline gathers, the elastic members 100 for the leg hole gathers, the elastic members 90W2 for the hip gathers, the elastic members 91 for the rear waistline gathers, and the elastic members 92 for the leg hole gathers.

In step S102, the leg hole opening P is formed by cutting together the center sheet 50, the front waistline sheet 60, and the rear waistline sheet 70 in the predetermined shape.

In step S103, the absorbent body 2 is arranged between the leg hole openings P formed in step S102.

In step S104, after folding the front waistline sheet 60 towards the rear waistline sheet 70, the front waistline sheet 60 and the rear waistline sheet 70 are joined.

In step S105, by cutting the both-side edges of the joined portion of the front waistline sheet 60 and the both-side edges of the rear waistline sheet 70, the absorbent article 1 is generated.

According to the absorbent article 1 of the present embodiment, wrinkles caused in the absorbent body 2 arranged in the front waistline portion S10A can be reduced while improving a contact of the absorbent body 2 arranged in the rear waistline portion S10B to the wearer.

(First Modification)

With reference to FIGS. 8(a) to 8(c), the absorbent article 1 according to a first modification of the present invention will be described. Hereinafter, the absorbent article 1 according to the present modification will be described while focusing on the differences from the absorbent article 1 according to the aforementioned first embodiment. Note that the other parts except the differences are identical to those in the aforementioned first embodiment.

In the absorbent article 1 according to the first modification, a shape of the joining portion H between the chassis 3 and the absorbent body 2 is such as shown in FIG. 8(a) to FIG. 8(c).

Figure 8:
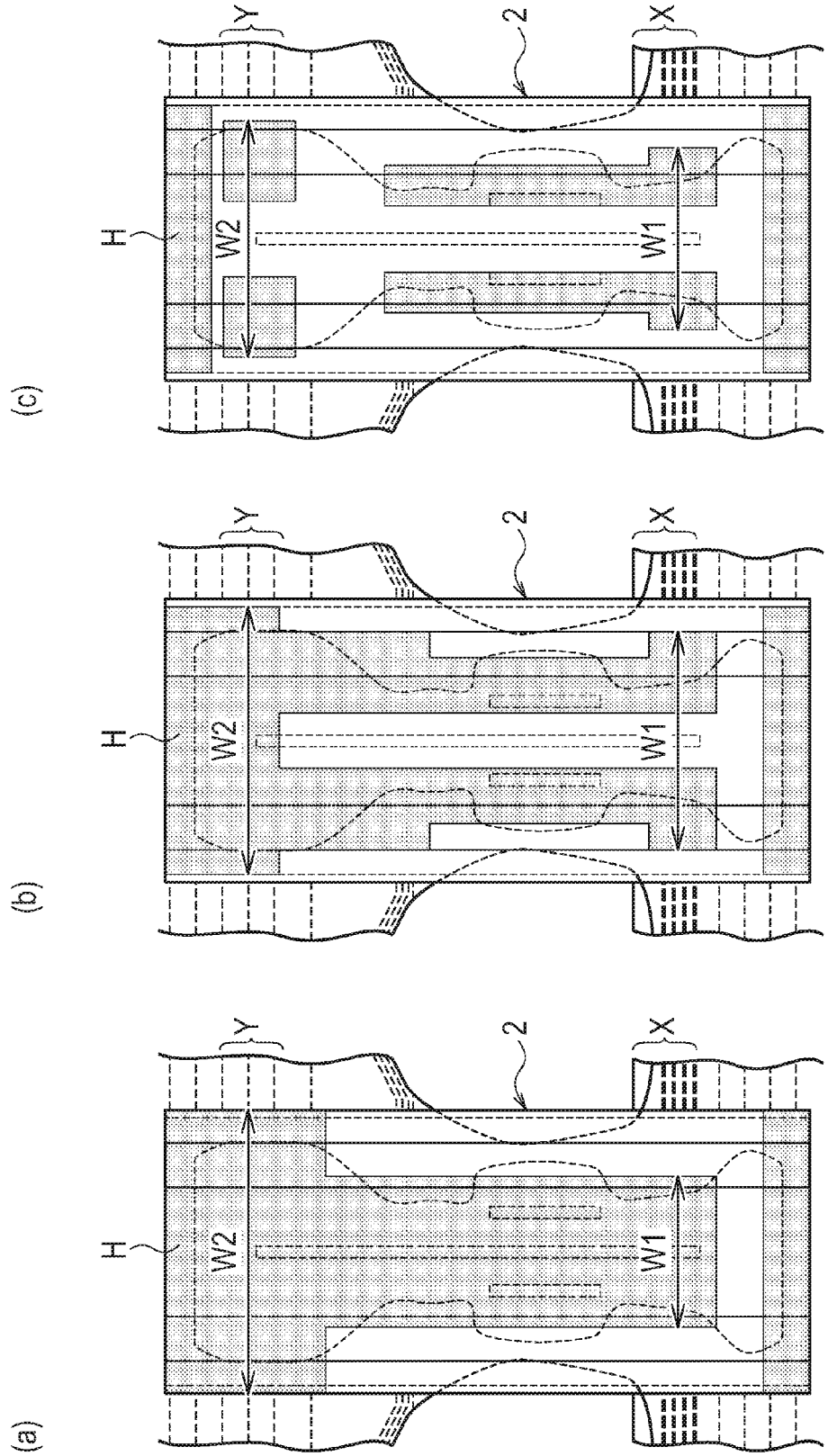
FIG. 8(*a*) to FIG. 8(*c*) are plan views of an absorbent article according to a first modification of the present invention.

That is, the absorbent article 1 according to the first modification, as shown in FIG. 8(*a*), the chassis 3 and the absorbent body 2 may be joined together at the entire region inside the joining portion H.

Further, in the absorbent article 1 according to the first modification 1, as shown in FIG. 8(*b*) and FIG. 8(*c*), the joining portion H may be configured by a plurality of joining portions H which are separated from each other.

The absorbent article 1 according to the first modification is also configured so that, in the width direction W, the length W1 of the joining portion H between the chassis 3 and the absorbent body 2 at the first portion X is shorter than the length W2 of the joining portion H between the chassis 3 and the absorbent body 2 at the second portion Y.

(Second Modification)

Further, the chassis 3 and the absorbent body 2 may be configured differently from those of the absorbent article 1 according to the aforementioned first embodiment. Note that the other parts except these differences are identical to those in the aforementioned embodiment.

Figure 9:
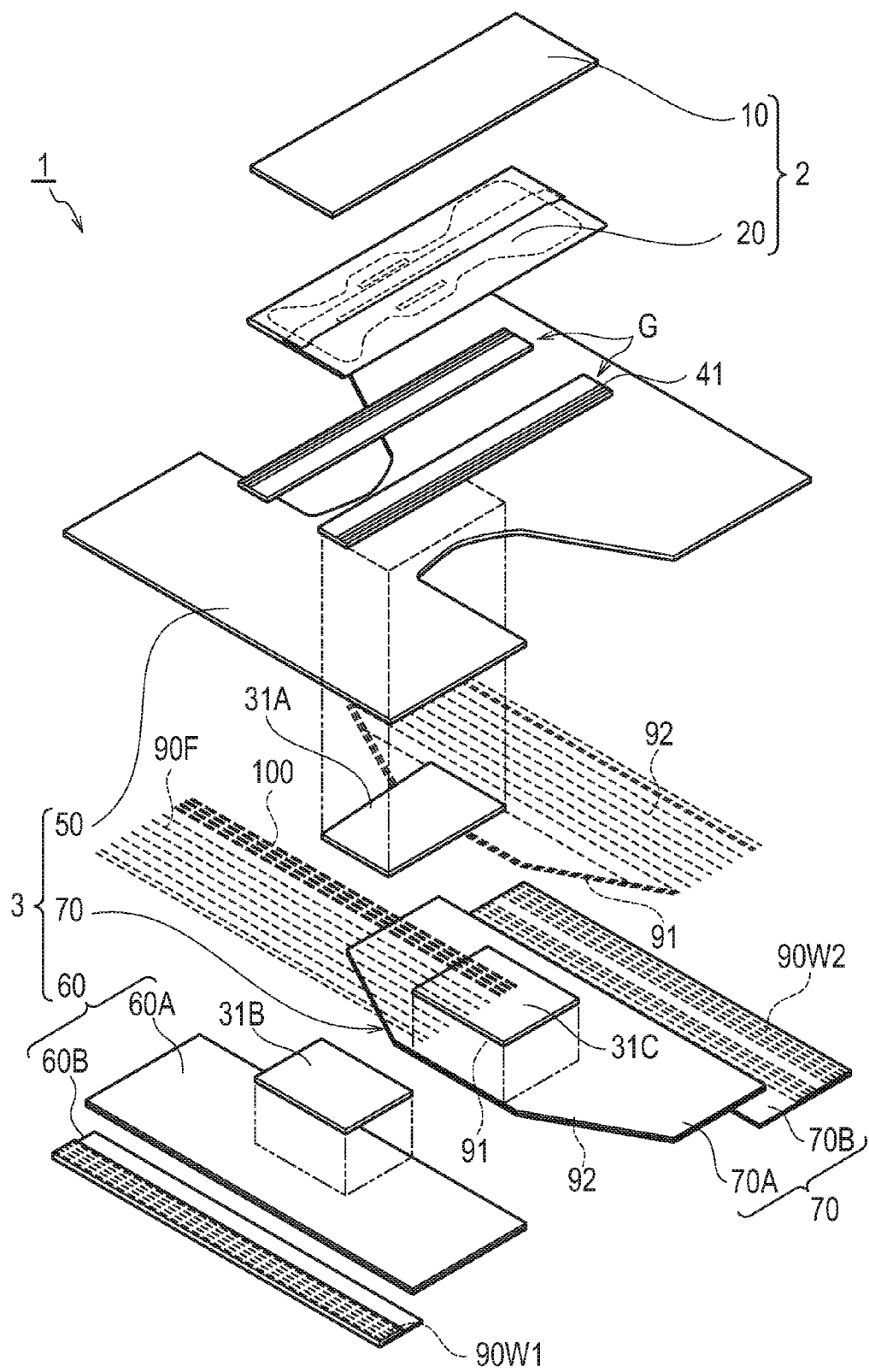
FIG. 9 is an exploded view of an absorbent article according to a second modification of the present invention.

For example, as shown in FIG. 9, instead of the absorbent body-side backsheet 30 that is provided inside the absorbent body 2 in the absorbent article 1 according to the first embodiment, leakage-preventing films 31A to 31C may be provided at the chassis 3 side as the leakage-preventing film that must be provided at the skin non-contact surface side of the absorbent article 1 of the absorbent core 20.

Note that in the example shown in FIG. 9, the front waistline sheet 60 is configured by a sheet 60A and a sheet 60B, and the rear waistline sheet 70 is configured by a sheet 70A and a sheet 70B.

In the absorbent article 1 having the configuration, the absorbent body 2 is configured by the absorbent core 20 and the absorbent body-side topsheet 10.

Further, the chassis 3 and the absorbent body 2 may even be integrated. In the absorbent article 1 having the configuration, the absorbent body 2 is configured by the absorbent core 20. That is, the absorbent body-side topsheet 10 and the absorbent body-side backsheet 30 are not included in the absorbent body 1.

Thus, the present invention has been explained in detail by using the above-described embodiments; however, it is obvious that for persons skilled in the art, the present invention is not limited to the embodiments explained herein. The present invention can be implemented as corrected and modified modes without departing from the gist and the scope of the present invention defined by the claims. Therefore, the description of the specification is intended for explaining the example only and does not impose any limited meaning to the present invention.

In addition, the entire content of Japanese Patent Application No. 2010-096531 (filed on Apr. 19, 2010) is incorporated in the present specification by reference.

INDUSTRIAL APPLICABILITY

According to the present invention, it is possible to provide the absorbent article which is capable of reducing wrinkles caused in the absorbent body arranged in the front waistline portion while increasing a contact of the absorbent body arranged in the rear waistline portion to the wearer.

REFERENCE SIGNS LIST

1 . . . Absorbent article
S10A . . . Front waistline portion
S10B . . . Rear waistline portion
S10B1 . . . Hip portion
S10B2 . . . Leg hole portion
S20 . . . Crotch portion
X . . . First portion
Y . . . Second portion
2 . . . Absorbent body
3 . . . Chassis
90W1, 90W2 . . . Elastic members for the hip gathers
90F . . . Elastic members for the front waistline gathers
91 . . . Elastic members for the rear waistline gathers
92, 100 . . . Elastic members for the leg hole gathers

The invention claimed is:

1. An absorbent article, comprising:
a chassis; and
an absorbent body, wherein
the chassis includes a front waistline portion, a rear waistline portion, and a crotch portion provided between the front waistline portion and the rear waistline portion,
each of the front and rear waistline portions has side edges opposite each other in a width direction of the absorbent article,
the absorbent body has lateral edges opposite each other in the width direction,
the side edges of the front waistline portion and the side edges of the rear waistline portion are joined to each other to define leg hole openings,
the absorbent body extends, in a longitudinal direction of the absorbent article, from the crotch portion into the front waistline portion and the rear waistline portion,
the front waistline portion includes a first portion provided at a leg hole opening side of a portion at which the side edges of the front and rear waistline portions are joined, and extending from one edge of the side edges of the front waistline portion to the other edge in the width direction,
the rear waistline portion includes a second portion opposed to the first portion,
the first portion includes a first elastic member that extends in a straight line in the width direction,
the second portion includes a second elastic member that extends in a straight line in the width direction,
an extension stress applied in the width direction by the first elastic member to the first portion is larger than an extension stress applied in the width direction by the second elastic member to the second portion,
the chassis and the absorbent body are joined to each other at a first joining portion, a second joining portion, and a third joining portion,
the first joining portion is arranged, in the longitudinal direction, between the second joining portion and the third joining portion,
the third joining portion is arranged closer to a front edge of the front waistline portion in the longitudinal direction than the first joining portion,
in a developed condition that is free of the extension stresses of the first and second elastic members applied to the first and second portions, respectively, a width of the first joining portion in the width direction at the first portion is smaller than
(i) a width of the second joining portion in the width direction at the second portion and
(ii) a width of the third joining portion in the width direction,
a length of the third joining portion in the longitudinal direction is smaller than a length of the second joining portion in the longitudinal direction, an extension stress of the first portion between the lateral edges of the absorbent body in the width direction is smaller than an extension stress of the first portion outside the lateral edges of the absorbent body in the width direction, and the extension stress of the first portion outside the lateral edges of the absorbent body in the width direction is larger than an extension stress of the second portion outside the lateral edges of the absorbent body in the width direction.

2. The absorbent article according to claim 1, wherein the absorbent body has front and rear edges opposite each other in the longitudinal direction of the absorbent article, and a distance between an edge of the first portion at the leg hole opening side and the front edge of the absorbent body within the front waistline portion is longer than a distance between an edge of the second portion at the leg hole opening side and the rear edge of the absorbent body within the rear waistline portion.

3. The absorbent article according to claim 1, wherein the front waistline portion further comprises a further elastic member extending across the absorbent body in the width direction, and located forward of the first portion in the longitudinal direction, wherein an extension stress of a portion of the front waistline portion where said further elastic member is located is smaller than the extension stress of the first portion.

4. The absorbent article according to claim 1, wherein the rear waistline portion has a hip portion where the side edges of the rear waistline portion are correspondingly joined with the side edges of the front waistline portion, the hip portion extending in the width direction from one edge of the side edges of the rear waistline portion to the other edge, and a leg hole portion positioned closer to the crotch portion than the hip portion.

5. The absorbent article according to claim 4, wherein the leg hole portion includes a leg hole elastic member extending along an edge of the leg hole portion at the leg hole opening side, and an extension stress of the first portion is larger than an extension stress of a portion of the leg hole portion where the leg hole elastic member is located.

6. The absorbent article according to claim 4, wherein the second elastic member overlaps the leg hole elastic member.

7. The absorbent article according to claim 1, wherein the first elastic member extends continuously from one edge of the side edges of the front waistline portion to the other edge of the side edges in the front waistline portion in the width direction.

8. The absorbent article according to claim 7, wherein the second elastic members extends continuously from one edge of the side edges of the rear waistline portion to the other edge of the side edges in the rear waistline portion in the width direction.

9. The absorbent article according to claim 1, wherein the first portion further includes a pair of clothing fabrics sandwiching the first elastic member therebetween, the second portion further includes a pair of clothing fabrics sandwiching the second elastic member therebetween, and the extension stress of the first portion, including the first elastic member and the corresponding pair of clothing fabrics, outside the lateral edges of the absorbent body in the width direction is larger than the extension stress of the second portion, including the second elastic member and the corresponding pair of clothing fabrics, outside the lateral edges of the absorbent body in the width direction.

10. The absorbent article according to claim 1, wherein the absorbent body has front and rear edges opposite each other in the longitudinal direction, and the first portion extends from an edge of the leg hole opening in the front waistline portion toward and terminates before the front edge of the absorbent body in the longitudinal direction.

11. The absorbent article according to claim 1, wherein the third joining portion is spaced, in the longitudinal direction, away from the first elastic member in the first portion at the front waistline portion, and the first joining portion overlaps the first elastic member in the first portion in a thickness direction of the absorbent article.

* * * * *